United States Patent
Muratoglu et al.

(10) Patent No.: US 7,304,097 B2
(45) Date of Patent: *Dec. 4, 2007

(54) HIGH MODULUS CROSSLINKED POLYETHYLENE WITH REDUCED RESIDUAL FREE RADICAL CONCENTRATION PREPARED BELOW THE MELT

(75) Inventors: Orhun K. Muratoglu, Cambridge, MA (US); Stephen H. Spiegelberg, Winchester, MA (US); Gareth H. McKinley, Acton, MA (US)

(73) Assignees: Massachusetts General Hospital, Boston, MA (US); Cambridge Polymer Group, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/464,872

(22) Filed: Aug. 16, 2006

(65) Prior Publication Data

US 2007/0004818 A1   Jan. 4, 2007

Related U.S. Application Data

(63) Continuation of application No. 11/030,115, filed on Jan. 7, 2005, now Pat. No. 7,166,650, which is a continuation of application No. 10/252,582, filed on Sep. 24, 2002, now Pat. No. 6,852,772.

(60) Provisional application No. 60/344,354, filed on Jan. 4, 2002.

(51) Int. Cl.
*C08F 2/46* (2006.01)
*A61F 2/28* (2006.01)
*A61F 2/30* (2006.01)
*A61F 2/32* (2006.01)

(52) U.S. Cl. .............. 522/161; 522/125; 522/150; 522/184; 522/189; 522/157; 523/115; 523/113; 526/352; 526/352.2; 526/72; 526/73; 526/348; 623/11.11; 623/16.11; 623/13.12; 623/18.11; 623/21.11; 623/21.21

(58) Field of Classification Search ............ 522/150, 522/161, 157, 184, 189, 125, 113, 114; 523/113; 523/115; 526/352, 352.2, 72, 73, 348; 623/11.11, 623/13.12, 18.11, 22.11, 22.21, 18, 22

See application file for complete search history.

(56) References Cited

U.S. PATENT DOCUMENTS

| | | | |
|---|---|---|---|
| 4,113,595 A | 9/1978 | Hagiwara et al. | 204/159.17 |
| 4,587,163 A | 5/1986 | Zachariades | 428/292 |
| 5,030,402 A | 7/1991 | Zachariades | 264/138 |
| 5,414,049 A | 5/1995 | Sun et al. | 525/333.7 |
| 5,428,079 A | 6/1995 | Bastiaansen et al. | 522/161 |
| 5,449,745 A | 9/1995 | Sun et al. | 528/483 |
| 5,508,319 A | 4/1996 | DeNicola et al. | 522/161 |
| 5,543,471 A | 8/1996 | Sun et al. | 525/333.7 |
| 5,577,368 A | 11/1996 | Hamilton et al. | 53/432 |
| 5,594,041 A | 1/1997 | Dearnaley et al. | 522/2 |
| 5,650,485 A | 7/1997 | Sun et al. | 528/483 |
| 5,728,748 A | 3/1998 | Sun et al. | 522/65 |
| 5,753,182 A | 5/1998 | Higgins | 422/23 |
| 5,824,411 A | 10/1998 | Shalaby et al. | 428/364 |
| 5,834,113 A | 11/1998 | Shalaby et al. | 428/364 |
| 5,879,400 A | 3/1999 | Merrill et al. | 623/22 |
| 6,017,975 A | 1/2000 | Saum et al. | 522/161 |
| 6,143,232 A | 11/2000 | Rohr | 264/460 |
| 6,165,220 A | 12/2000 | McKellop et al. | 623/18 |
| 6,168,626 B1 | 1/2001 | Hyon et al. | 623/18.11 |
| 6,174,934 B1 | 1/2001 | Sun et al. | 523/113 |
| 6,184,265 B1 | 2/2001 | Hamilton et al. | 522/189 |
| 6,228,900 B1 | 5/2001 | Shen et al. | 522/153 |
| 6,242,507 B1 | 6/2001 | Saum et al. | 522/161 |
| 6,281,264 B1 | 8/2001 | Salovey et al. | 523/115 |
| 6,316,158 B1 | 11/2001 | Saum et al. | 430/130 |
| 6,395,799 B1 | 5/2002 | Johnson | 522/161 |
| 6,464,926 B1 | 10/2002 | Merrill et al. | 264/485 |
| 6,852,772 B2 | 2/2005 | Muratoglu et al. | 522/161 |
| 2001/0027345 A1 | 10/2001 | Merrill et al. | |
| 2005/0124718 A1 | 6/2005 | Muratogiu et al. | |

*Primary Examiner*—Sanza L. McClendon
(74) *Attorney, Agent, or Firm*—Proskauer Rose LLP

(57) ABSTRACT

The present invention provides an irradiated crosslinked polyethylene containing reduced free radicals, preferably containing substantially no residual free radical. Disclosed is a process of making irradiated crosslinked polyethylene by irradiating the polyethylene in contact with a sensitizing environment at an elevated temperature that is below the melting point, in order to reduce the concentration of residual free radicals to an undetectable level. A process of making irradiated crosslinked polyethylene composition having reduced free radical content, preferably containing substantially no residual free radicals, by mechanically deforming the polyethylene at a temperature that is below the melting point of the polyethylene, optionally in a sensitizing environment, is also disclosed herein.

44 Claims, 2 Drawing Sheets

HIGH MODULUS CROSSLINKED POLYETHYLENE WITH REDUCED RESIDUAL FREE RADICAL CONCENTRATION PREPARED BELOW THE MELT

This application is a continuation of U.S. Ser. No. 11/030,115, filed Jan. 7, 2005, now U.S. Pat. No. 7,166,650, which is a continuation of U.S. Ser. No. 10/252,582, filed Sep. 24, 2002, now U.S. Pat. No. 6,852,772 which claims priority to U.S. Ser. No. 60/344,354, filed Jan. 4, 2002, the entireties of which are hereby incorporated by reference.

The present invention relates to irradiated crosslinked polyethylene (PE) compositions having reduced free radical content, preferably containing reduced or substantially no residual free radicals, and processes of making crosslinked polyethylene. The processes can comprise the steps of irradiating the polyethylene while it is in contact with a sensitizing environment at an elevated temperature that is below the melting point in order to reduce the concentration of residual free radicals, preferably to an undetectable level. The invention also relates to processes of making crosslinked polyethylene having reduced free radical content, preferably containing substantially no residual free radicals, by mechanically deforming the irradiated PE either with or without contact with sensitizing environment during irradiation, at a temperature that is below the melting point of the polyethylene. These processes are complementary and can be used together or separately.

DESCRIPTION OF THE FIELD

Increased crosslink density in polyethylene is desired in bearing surface applications for joint arthroplasty because it significantly increases the wear resistance of this material. The preferred method of crosslinking is by exposing the polyethylene to ionizing radiation. However, ionizing radiation, in addition to crosslinking, also will generate residual free radicals, which are the precursors of oxidation-induced embrittlement. This is known to adversely affect in vivo device performance. Therefore, it is desirable to reduce the concentration of residual free radicals preferably to undetectable levels, following irradiation to avoid long-term oxidation.

In the past, in order to substantially reduce the concentration of residual free radicals in irradiated polyethylene, the polyethylene has to be heated to above its melting temperature (for example, about 140° C.). Melting frees or eliminates the crystalline structure, where the residual free radicals are believed to be trapped. This increase in the free radical mobility facilitates the recombination reactions, through which the residual free radical concentration can be markedly reduced. This technique, while effective at recombining the residual free radicals, has been shown to decrease the final crystallinity of the material. This loss of crystallinity will reduce the modulus of the polyethylene. Yet for high stress applications, such as unicompartmental knee designs, thin polyethylene tibial knee inserts, low conformity articulations, etc., high modulus is desired to minimize creep.

It is therefore desirable to reduce the residual free radical concentration without heating above the melting point in order to avoid significantly reducing the crystallinity of polyethylene, so as to permit insubstantial lowering, substantial maintenance, or an increase in the modulus.

SUMMARY OF THE INVENTION

An object of the invention to provide an improved irradiated crosslinked polyethylene having reduced concentration of free radicals, made by the process comprising irradiating the polyethylene at a temperature that is below the melting point of the polyethylene, optionally while it is in contact with a sensitizing environment, in order to reduce the content of free radicals, preferably to an undetectable level, optionally through mechanical deformation.

In accordance with one aspect of the present invention, there is provided an irradiated crosslinked polyethylene wherein crystallinity of the polyethylene is at least about 51% or more.

In accordance with another aspect of the present invention, there is provided an irradiated crosslinked polyethylene, wherein the elastic modulus of the polyethylene is higher or just slightly lower than, i.e. about equal to, that of the starting unirradiated polyethylene or irradiated polyethylene that has been subjected to melting.

According to the present invention, the polyethylene is a polyolefin and preferably is selected from a group consisting of a low-density polyethylene, high-density polyethylene, linear low-density polyethylene, ultra-high molecular weight polyethylene (UHMWPE), or mixtures thereof.

In one aspect of the present invention, the polyethylene is contacted with a sensitizing environment prior to irradiation. The sensitizing environment, for example, can be selected from the group consisting of acetylene, chloro-trifluoro ethylene (CTFE), trichlorofluoroethylene, ethylene or the like, or a mixture thereof containing noble gases, preferably selected from a group consisting of nitrogen, argon, helium, neon, and any inert gas known in the art. The gas can be a mixture of acetylene and nitrogen, wherein the mixture comprising about 5% by volume acetylene and about 95% by volume nitrogen, for example.

In one aspect of the invention, the starting material of the polyethylene can be in the form of a consolidated stock or the starting material can be also in the form of a finished product.

In another aspect of the invention, there is provided an irradiated crosslinked polyethylene with reduced free radical concentration, preferably with no detectable residual free radicals (that is, the content of free radicals is below the current detection limit of $10^{14}$ spins/gram), as characterized by an elastic modulus of about equal to or slightly higher than that of the starting unirradiated polyethylene or irradiated polyethylene that has been subject to melting. Yet in another aspect of the invention, there is provided a crosslinked polyethylene with reduced residual free radical content that is characterized by an improved creep resistance when compared to that of the starting unirradiated polyethylene or irradiated polyethylene that has been subjected to melting.

In accordance with one aspect of the invention there is provided a method of making a crosslinked polyethylene comprising irradiating the polyethylene at a temperature that is below the melting point of the polyethylene while it is in contact with a sensitizing environment in order to reduce the content of free radicals, preferably to an undetectable level.

In accordance with another aspect of the invention, there are provided methods of treating crosslinked polyethylene, wherein crystallinity of the polyethylene is about equal to that of the starting unirradiated polyethylene, wherein crystallinity of the polyethylene is at least about 51% or more, wherein elastic modulus of the polyethylene is about equal to or higher than that of the staring unirradiated polyethylene or irradiated polyethylene that has been subject to melting.

There also is provided a method of making a crosslinked polyethylene, wherein the annealing temperature is below the melting point of the polyethylene, wherein the annealing temperature is less than about 145° C., preferably less than about 140° C. and more preferably less than about 137° C.

Also provided herein, the material resulting from the present invention is a polyethylene subject to ionizing radiation with reduced free radical concentration, preferably containing substantially no residual free radicals, achieved through post-irradiation annealing at below the melting point at less than 145° C., preferably at less than 140° C. and more preferably at less than 137° C., in the presence of a sensitizing environment.

In one aspect of the invention, there is provided a method of making a crosslinked polyethylene, wherein the polyethylene is contacted with a sensitizing environment prior to irradiation.

In another aspect according to the present invention, there is provided a method of making a crosslinked polyethylene, wherein the sensitizing environment is acetylene, chlorotrifluoro ethylene (CTFE), trichlorofluoroethylene, ethylene gas, or mixtures of gases thereof, wherein the gas is a mixture of acetylene and nitrogen, wherein the mixture comprises about 5% by volume acetylene and about 95% by volume nitrogen.

Yet in another aspect according to the present invention, there is provided a method of making a crosslinked polyethylene, wherein the sensitizing environment is dienes with different number of carbons, or mixtures of liquids and/or gases thereof.

One aspect of the present invention is to provide a method of making a crosslinked polyethylene, wherein the irradiation is carried out using gamma radiation or electron beam radiation, wherein the irradiation is carried out at an elevated temperature that is below the melting temperature, wherein radiation dose level is between about 1 and about 10,000 kGy.

In one aspect there is provided a method of making a crosslinked polyethylene, wherein the annealing in the presence of sensitizing environment is carried out at above an ambient atmospheric pressure of at least about 1.0 atmosphere (atm) to increase the diffusion rate of the sensitizing molecules into polyethylene.

In another aspect there is provided a method, wherein the annealing in the presence of sensitizing environment is carried with high frequency sonication to increase the diffusion rate of the sensitizing molecules into polyethylene.

Yet in another aspect there is provided a method of treating irradiated crosslinked polyethylene comprising steps of contacting the polyethylene with a sensitizing environment; annealing at a temperature that is below the melting point of the polyethylene; and elevating the temperature that is below the melting point in presence of a sensitizing environment in order to reduce the concentration of residual free radicals, preferably to an undetectable level.

Another aspect of the invention provides an improved irradiated crosslinked polyethylene composition having reduced free radical concentration, made by the process comprising irradiating at a temperature that is below the melting point of the polyethylene, optionally in a sensitizing environment; mechanically deforming the polyethylene in order to reduce the concentration of residual free radical and optionally annealing below the melting point of the polyethylene, preferably at about 135° C., in order to reduce the thermal stresses.

In accordance with one aspect of the invention, mechanical deformation of the polyethylene is performed in presence of a sensitizing environment at an elevated temperature that is below the melting point of the polyethylene, wherein the polyethylene has reduced free radical content and preferably has no residual free radicals detectable by electron spin resonance.

In accordance with another aspect of the invention the irradiation is carried out in air or inert environment selected from a group consisting of nitrogen, argon, helium, neon, and any inert gas known in the art.

In accordance with still another aspect of the invention, the mechanical deformation is uniaxial, channel flow, uniaxial compression, biaxial compression, oscillatory compression, tension, uniaxial tension, biaxial tension, ultrasonic oscillation, bending, plane stress compression (channel die) or a combination of any of the above and performed at a temperature that is below the melting point of the polyethylene in presence or absence of a sensitizing gas.

Yet in accordance with another aspect of the invention, mechanical deformation of the polyethylene is conducted at a temperature that is less than the melting point of the polyethylene and above room temperature, preferably between about 100° C. and about 137° C., more preferably between about 120° C. and about 137° C., yet more preferably between about 130° C. and about 137° C., and most preferably at about 135° C.

In one aspect, the annealing temperature of the irradiated crosslinked polyethylene is below the melting point of the polyethylene, preferably less than about 145° C., more preferably less than about 140° C., and yet more preferably less than about 137° C.

Yet in another aspect, thee is provided an irradiated crosslinked polyethylene, wherein elastic modulus of the polyethylene is about equal to or higher than that of the starting unirradiated polyethylene.

In accordance with the present invention, there is provided a method of making an irradiated crosslinked polyethylene comprising irradiating at a temperature that is below the melting point of the polyethylene, optionally in a sensitizing environment, mechanically deforming the polyethylene in order to reduce the concentration of residual free radical and optionally annealing below the melting point of the polyethylene, preferably at about 135° C., in order to reduce the thermal stresses.

In accordance with one aspect of the invention, there is provided a method of mechanical deformation of polyethylene, optionally in presence of a sensitizing environment, at an elevated temperature that is below the melting point of the polyethylene, preferably at about 135° C., wherein the polyethylene has reduced free radical content and preferably has no residual free radical detectable by electron spin resonance.

In accordance with another aspect of the invention, there is provided a method of deforming polyethylene, wherein the temperature is less than the melting point of the polyethylene and above room temperature, preferably between about 100° C. and about 137° C., more preferably between about 120° C. and about 137° C., yet more preferably between about 130° C. and about 137° C., and most preferably at about 135° C.

Yet in another aspect of the present invention, there is provided a method of treating irradiated crosslinked polyethylene composition in order to reduce the residual free radicals comprising steps of: mechanically deforming the polyethylene; and annealing at a temperature that is below the melting point of the polyethylene in order to reduce the thermal stresses, wherein the mechanical deformation is performed (preferably at about 135° C.), optionally in presence of a sensitizing environment.

Still in another aspect of the invention, there is provided an irradiated crosslinked polyethylene composition made by the process comprising steps of: irradiating at a temperature that is below the melting point of the polyethylene; mechanically deforming the polyethylene below the melting point of the irradiated polyethylene in order to reduce the concentration of residual free radicals; annealing at a temperature above the melting point; and cooling down to room temperature.

In another aspect, the invention provides a method of making an irradiated crosslinked polyethylene composition comprising steps of: mechanically deforming the polyethylene at a solid- or a molten-state; crystallizing/solidifying the polyethylene at the deformed state; irradiating the polyethylene below the melting point of the polyethylene; and heating the irradiated polyethylene below the melting point in order to reduce the concentration of residual free radicals and to recover the original shape or preserve shape memory.

Still in another aspect, the invention provides an irradiated crosslinked polyethylene composition made by the process comprising steps of: mechanically deforming the polyethylene at a solid- or a molten-state; crystallizing/solidifying the polyethylene at the deformed state; irradiating the polyethylene below the melting point of the polyethylene; and heating the irradiated polyethylene below the melting point in order to reduce the concentration of residual free radicals and to recover the original shape or preserve shape memory.

Still in another aspect, the invention provides an irradiated crosslinked polyethylene with substantially reduced or no detectable residual free radicals, wherein crystallinity of the polyethylene is about 51% or greater.

These and other aspects of the present invention will become apparent to the skilled person in view of the description set forth below.

BRIEF DESCRIPTION OF THE DRAWINGS

FIG. 1 shows schematically the channel die set-up used in preparing some of the samples described in the Examples disclosed herein. The test sample A is first heated to a desired temperature along with the channel die B. The channel die B is then placed in a compression molder and the heated sample A is placed and centered in the channel. The plunger C, which is also preferably heated to the same temperature, is placed in the channel. The sample A is then compressed by pressing the plunger C to the desired compression ratio. The flow direction (FD), wall direction (WD), and compression direction (CD) are as marked.

FIG. 2 shows schematically the oxidative aging or accelerated aging process and determination of residual free radicals thereafter. A specimen is prepared by cutting a 3 mm by 3 mm by 10 mm piece near the body center with long axis of the specimen in the flow direction of the channel die (see A). The specimen is then analyzed with electron spin resonance for residual free radicals. The remaining half of the test sample is further machine to obtain a cube with dimensions of 1 cm by 1 cm by 1 cm. This cubic specimen (see B) is then subjected to thermo-oxidative aging or accelerated aging in air convection oven at 80° C. for three weeks. This method of aging will induce oxidation in the polyethylene if there are residual free radicals. At the completion of the aging, the cubic specimen is cut in half and microtomed to remove a 200 micrometer thin section. The section is then analyzed using a BioRad UMA500 infra-red microscope as a function of depth away from the edge of the microtomed section as shown with arrow in the figure.

DETAILED DESCRIPTION OF THE INVENTION

Figure 1:
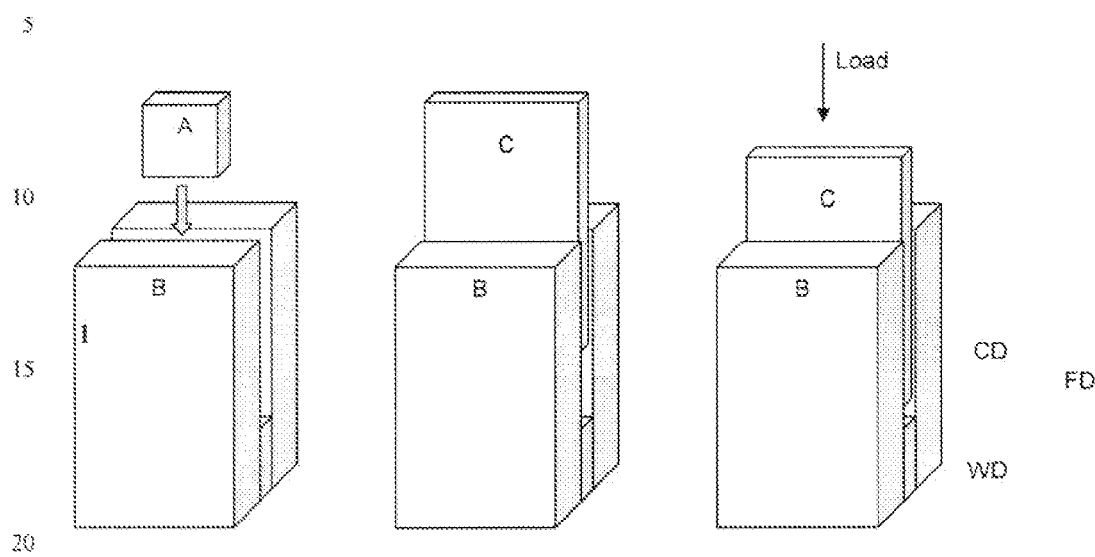
FIG. 1.

The present invention describes methods that allow reduction in the concentration of residual free radicals in irradiated polyethylene, preferably to undetectable levels, without heating the material above its melting point. This method involves contacting the irradiated polyethylene with a sensitizing environment, and heating the polyethylene to above a critical temperature that allows the free radicals to react with the sensitizing environment, but is still below the melting point. It is likely that this critical temperature corresponds to the alpha transition of the polyethylene. The alpha transition of polyethylene is normally around 90-95° C.; however, in the presence of a sensitizing environment that is soluble in polyethylene, the alpha transition may be depressed. The alpha transition is believed to induce motion in the crystalline phase, which is believed to increase the diffusion of the sensitizing environment into this phase and/or release the trapped free radicals. The free radicals can now react with the sensitizing gas and/or liquid, which are though to act as a linking agent between adjacent free radicals.

The material resulting from the present invention is a crosslinked polyethylene that has reduced residual free radicals, and preferably no detectable free radicals, while not substantially compromising the crystallinity and modulus.

According to the invention, the polyethylene is irradiated in order to crosslink the polymer chains. In general, gamma irradiation gives a high penetration depth but takes a longer time, resulting in the possibility of some oxidation. In general, electron irradiation gives more limited penetration depths but takes a shorter time, and hence the possibility of oxidation is reduced. The irradiation dose can be varied to control the degree of crosslinking and crystallinity in the final polyethylene product. Preferably, a dose of greater than about 1 kGy is used, more preferably a dose of greater than about 20 kGy is used. When electron irradiation is used, the energy of the electrons can be varied to change the depth of penetration of the electrons, thereby controlling the degree of penetration of crosslinking in the final product. Preferably, the energy is about 0.5 MeV to about 10 MeV, more preferably about 5 MeV to about 10 MeV. Such variability is particularly useful, when the irradiated object is an article of varying thickness or depth, for example, an articular cup for a medical prosthesis.

The invention also provides an improved irradiated crosslinked polyethylene, containing reduced free radical concentration and preferably containing substantially no detectable free radicals, made by the process comprising steps of contacting the irradiated polyethylene with a sensitizing environment; annealing at a temperature that is below the melting point of the polyethylene; and elevating to a temperature that is below the melting point in presence of a sensitizing environment in order to reduce the concentration of residual free radicals, preferably to an undetectable level.

The present invention provides methods of treating polyethylene, wherein crystallinity of the polyethylene is higher than that of the starting unirradiated polyethylene or irradiated polyethylene that has been melted, wherein crystallinity of the polyethylene is at least about 51%, wherein elastic modulus of the polyethylene is about the same as or is higher than that of the starting unirradiated polyethylene.

The present invention also describes methods that allow reduction in the concentration of residual free radical in irradiated polyethylene, even to undetectable levels, without heating the material above its melting point. This method involves subjecting an irradiated sample to a mechanical deformation that is below the melting point. The deformation temperature could be as high as about 135° C. The deformation causes motion in the crystalline lattice, which permits recombination of free radicals previously trapped in the lattice through crosslinking with adjacent chains or formation of trans-vinylene unsaturations along the backbone of the same chain. If the deformation is of sufficiently small amplitude, plastic flow can be avoided. The percent crystallinity should not be compromised as a result. Additionally, it is possible to perform the mechanical deformation on machines components without loss in mechanical tolerance. The material resulting from the present invention is a crosslinked polyethylene that has reduced concentration of residuals free radical, and preferably substantially no detectable free radicals, while not substantially compromising the crystallinity and modulus.

The present invention further describes that the deformation can be of large magnitude, for example, a compression ratio of 2 in a channel die. The deformation can provide enough plastic deformation to mobilize the residual free radicals that are trapped in the crystalline phase. It also can induce orientation in the polymer that can provide anisotropic mechanical properties, which can be useful in implant fabrication. If not desired, the polymer orientation can be removed with an additional step of annealing at an increased temperature below or above the melting point.

According to another aspect of the invention, a high strain deformation can be imposed on the irradiated component. In this fashion, free radicals trapped in the crystalline domains likely can react with free radicals in adjacent crystalline planes as the planes pass by each other during the deformation-induced flow. High frequency oscillation, such as ultrasonic frequencies, can be used to cause motion in the crystalline lattice. This deformation can be performed at elevated temperatures that is below the melting point of the polyethylene, and with or without the presence of a sensitizing gas. The energy introduced by the ultrasound yields crystalline plasticity without an increase in overall temperature.

The present invention also provides methods of further annealing following free radical elimination below melting point. According to the invention, elimination of free radicals below the melt is achieved either by the sensitizing gas methods and/or the mechanical deformation methods. Further annealing of crosslinked polyethylene containing reduced or no detectable residual free radicals is done for various reasons, for example.

1. Mechanical deformation, if large in magnitude (for example, a compression ratio of two during channel die deformation), will induce molecular orientation, which may not be desirable for certain applications, for example, acetabular liners. Accordingly, for mechanical deformation:
    a) Annealing below the melting point (for example, less than about 137° C.) is utilized to reduce the amount of orientation and also to reduce some of the thermal stresses that can persist following the mechanical deformation at an elevated temperature and cooling down. Following annealing, it is desirable to cool down the polyethylene at slow enough cooling rate (for example, at about 10° C.) so as to minimize thermal stresses. If under a given circumstance, annealing below the melting point is not sufficient to achieve reduction in orientation and/or removal of thermal stresses, one can heat the polyethylene to above its melting point.
    b) Annealing above the melting point (for example, more than about 137° C./hour) can be utilized to eliminate the crystalline matter and allow the polymeric chains to relax to a low energy, high entropy state. This relaxation will lead to the reduction of orientation in the polymer and will substantially reduce thermal stresses. Cooling down to room temperature is then carried out at a slow enough cooling rate (for example, at about 10° C./hour) so as to minimize thermal stresses.

2. The contact before, during, and/or after irradiation with a sensitizing environment to yield a polyethylene with no substantial reduction in its crystallinity when compared to the reduction in crystallinity that otherwise occurs following irradiation and subsequent melting. The crystallinity of polyethylene contacted with a sensitizing environment and the crystallinity of radiation treated polyethylene is reduced by annealing the polymer above the melting point (for example, more than about 137° C.). Cooling down to room temperature is then carried out at a slow enough cooling rate (for example, at about 10° C./hour) so as to minimize thermal stresses.

As described herein, it is demonstrated that mechanical deformation can eliminate residual free radicals in a radiation crosslinked UHMWPE. The invention also provides that one can first deform UHMWPE to a new shape either at solid- or at molten-state, for example, by compression. According to a process of the invention, mechanical deformation of UHMWPE when conducted at a molten-state, the polymer is crystallized under load to maintain the new deformed shape. Following the deformation step, the deformed UHMWPE sample is irradiated below the melting point to crosslink, which generates residual free radicals. To eliminate these free radicals, the irradiated polymer specimen is heated to a temperature below the melting point of the deformed and irradiated polyethylene (for example, up to about 135° C.) to allow for the shape memory to partially recover the original shape. Generally, it is expected to recover about 80-90% of the original shape. During this recovery, the crystals undergo motion, which can help the free radical recombination and elimination. The above process is termed as a 'reverse-IBMA'. The reverse-IBMA (reverse-irradiation below the melt and mechanical annealing) technology can be a suitable process in terms of brining the technology to large-scale production of UHMWPE-based medical devices.

These and other aspects of the present invention will become apparent to the skilled person in view of the description set forth below.

A "sensitizing environment" refers to a mixture of gases and/or liquids (at room temperature) that contain sensitizing gaseous and/or liquid component(s) that can react with residual free radicals to assist in the recombination of the residual free radicals. The gases maybe acetylene, chlorotrifluoro ethylene (CTFE), ethylene, or like. The gases or the mixtures of gases thereof may contain noble gases such as nitrogen, argon, neon and like. Other gases such as, carbon dioxide or carbon monoxide may also be present in the mixture. In applications where the surface of a treated material is machined away during the device manufacture, the gas blend could also contain oxidizing gases such as oxygen. The sensitizing environment can be dienes with different number of carbons, or mixtures of liquids and/or gases thereof. An example of a sensitizing liquid component is octadiene or other dienes, which can be mixed with other sensitizing liquids and/or non-sensitizing liquids such as a hexane or a heptane. A sensitizing environment can include a sensitizing gas, such as acetylene, ethylene, or a similar gas or mixture of gases, or a sensitizing liquid, for example, a diene. The environment is heated to a temperature ranging from room temperature to a temperature below the melting point of the material.

"Residual free radicals" refers to free radicals that are generated when a polymer is exposed to ionizing radiation such as gamma or e-beam irradiation. While some of the free radicals recombine with each other to form crosslinks, some become trapped in crystalline domains. The trapped free radicals are also known as residual free radicals.

The phrase "substantially no detectable residual free radical" refers to no detectable free radical or no substantial residual free radical, as measured by electron spin resonance (ESR). The lowest level of free radicals detectable with state-of-the-art instruments is about $10^{14}$ spins/gram and thus the term "detectable" refers to a detection limit of $10^{14}$ spins/gram by ESR.

The terms "about" or "approximately" in the context of numerical values and ranges refers to values or ranges that approximate or are close to the recited values or ranges such that the invention can perform as intended, such as having a desired degree of crosslinking and/or a desired lack of free radicals, as is apparent to the skilled person from the teachings contained herein. This is due, at least in part, to the varying properties of polymer compositions. Thus these terms encompass values beyond those resulting from systematic error.

The terms "alpha transition" refers to a transitional temperature and is normally around 90-95° C.; however, in the presence of a sensitizing environment that dissolves in polyethylene, the alpha transition may be depressed. The alpha transition is believed (An explanation of the "alpha transition temperature" can be found in *Anelastic and Dielectric Effects in Polymeric Solids*, pages 141-143, by N. G. McCrum, B. E. Read and G. Williams; J. Wiley and Sons, N.Y., N.Y., published 1967) to induce motion in the crystalline phase, which is hypothesized to increase the diffusion of the sensitizing environment into this phase and/or release the trapped free radicals.

The term "critical temperature" corresponds to the alpha transition of the polyethylene.

The term "below melting point" or "below the melt" refers to a temperature below the melting point of a polyethylene, for example, UHMWPE. The term "below melting point" or "below the melt" refers to a temperature less than 145° C., which may vary depending on the melting temperature of the polyethylene, for example, 145° C., 140° C. or 135° C., which again depends on the properties of the polyethylene being treated, for example, molecular weight averages and ranges, batch variations, etc. The melting temperature is typically measured using a differential scanning calorimeter (DSC) at a heating rate of 10° C. per minute. The peak melting temperature thus measured is referred to as melting point and occurs, for example, at approximately 137° C. for some grades of UHMWPE. It may be desirable to conduct a melting study on the starting polyethylene material in order to determine the melting temperature and to decide upon an irradiation and annealing temperature.

The term "pressure" refers to an atmospheric pressure, above the ambient pressure, of at least about 1 atm for annealing in a sensitizing environment.

The "annealing" refers to heating the polymer below its peak melting point. Annealing time can be at least 1 minute to several weeks long. In one aspect the annealing time is about 4 hours to about 48 hours, preferably 24 to 48 hours and more preferably about 24 hours. The annealing time required to achieve a desired level of recovery following mechanical deformation is usually longer at lower annealing temperatures. "Annealing temperature" refers to the thermal condition for annealing in accordance with the invention.

The term "contacted" includes physical proximity with or touching such that the sensitizing agent can perform its intended function. Preferably, a polyethylene composition or pre-form is sufficiently contacted such that it is soaked in the sensitizing agent, which ensures that the contact is sufficient. Soaking is defined as placing the sample in a specific environment for a sufficient period of time at an appropriate temperature. The environment include a sensitizing gas, such as acetylene, ethylene, or a similar gas or mixture of gases, or a sensitizing liquid, for example, a diene. The environment is heated to a temperature ranging from room temperature to a temperature below the melting point of the material. The contact period ranges from at least about 1 minute to several weeks and the duration depending on the temperature of the environment. In one aspect the contact time period at room temperature is about 24 hours to about 48 hours and preferably above 24 hours.

The term "Mechanical deformation" refers to a deformation taking place below the melting point of the material essentially 'cold-working' the material. The deformation modes include uniaxial, channel flow, uniaxial compression, biaxial compression, oscillatory compression, tension, uniaxial tension, biaxial tension, ultra-sonic oscillation, bending, plane stress compression (channel die) or a combination of any of the above. The deformation could be static or dynamic. The dynamic deformation can be a combination of the deformation modes in small or large amplitude oscillatory fashion. Ultrasonic frequencies can be used. All deformations can be performed in the presence of sensitizing gases and/or at elevated temperatures.

The term "deformed state" refers to a state of the polyethylene material following a deformation process, such as a mechanical deformation, as described herein, at solid or at melt. Following the deformation process, deformed polyethylene at a solid state or at melt is be allowed to solidify/crystallize while still maintains the deformed shape or the newly acquired deformed state.

"IBMA" refers to irradiation below the melt and mechanical annealing. "IBMA" was formerly referred to as "CIMA" (Cold Irradiation and Mechanically Annealed).

Sonication or ultrasonic at a frequency range between 10 and 100 kHz is used, with amplitudes on the order of 1-50 microns. The time of sonication is dependent on the frequency and temperature of sonication. In one aspect, sonication or ultrasonic frequency ranged from about 1 second to about one week, preferably about 1 hour to about 48 hours, more preferably about 5 hours to about 24 hours and yet more preferably about 12 hours.

By ultra-high molecular weight polyethylene (UHMWPE) is meant chains of ethylene that have molecular weights in excess of about 500,000 g/mol, preferably above about 1,000,000 g/mol, and more preferably above about 2,000,000 g/mol. Often the molecular weights can reach about 8,000,000 g/mol or more. By initial average molecular weight is meant the average molecular weight of the UHMWPE starting material, prior to any irradiation. See U.S. Pat. No. 5,879,400; PCT/US99/16070, filed on Jul. 16, 1999.

WO 20015337, and PCT/US97/02220, filed Feb. 11, 1997, WO 9729793, for properties of UHMWPE.

By "crystallinity" is meant the fraction of the polymer that is crystalline. The crystallinity is calculated by knowing the weight of the sample (weight in grams), the heat absorbed by the sample in melting (E, in J/g) and the heat of melting of polyethylene crystals ($\Delta H=291$ J/g), and using the following equation:

% Crystallinity=$E/w \cdot \Delta H$

By tensile "elastic modulus" is meant the ratio of the nominal stress to corresponding strain for strains as determined using the standard test ASTM 638 M III and the like or their successors.

The term "conventional UHMWPE" refers to commercially available polyethylene of molecular weights greater than about 500,000. Preferably, the UHMWPE starting material has an average molecular weight of greater than about 2 million.

By "initial average molecular weight" is meant the average molecular weight of the UHMWPE starting material, prior to any irradiation.

The term "interface" in this invention is defined as the niche in medical devices formed when an implant is in a configuration where the polyethylene is in functional relation with another piece (such as a metallic or a polymeric component), which forms an interface between the polymer and the metal or another polymeric material. For example, interfaces of polymer-polymer or polymer-metal in medical prosthesis such as, orthopedic joints and home replacement parts, e.g., hip, knee, elbow or ankle replacements. Medical implants containing factory-assembled pieces that are in intimate contact with the polyethylene form interfaces. In most cases, the interfaces are not accessible to the ethylene oxide (EtO) gas or the gas plasma (GP) during a gas sterilization process.

The piece forming an interface with polymeric material can be metallic. The metal piece in functional relation with polyethylene, according to the present invention, can be made of a cobalt chrome alloy, stainless steel, titanium, titanium alloy or nickel cobalt alloy, for example.

The products and processes of this invention also apply to various types of polymeric materials, for example, high-density-polyethylene, low-density-polyethylene, linear-low-density-polyethylene, UHMWPE, and polypropylene.

The invention is further demonstrated by the following example, which do not limit the invention in any manner.

EXAMPLES

Example 1

Channel Die Set-up in Sample Preparation

Referring to FIG. 1, a test sample "A" is first heated to a desired temperature along with the channel die B. The channel die 'B' is then placed in a compression molder and the heated sample A is placed and centered in the channel. The plunger 'C', which also is preferably heated to the same temperature, is placed in the channel. The sample 'A' is then compressed by pressing the plunger 'C' to the desired compression ratio. The sample will have an elastic recovery after removal of load on the plunger. The compression ratio, $\lambda$ (final height/initial height), of the test sample is measured after the channel die deformation following the elastic recovery. The flow direction (FD), wall direction (WD), and compression direction (CD) are as marked in FIG. 1.

Example 2

Warm Irradiation with Sensitizing Gas Below the Alpha Transition

Test samples or a finished medical product of ultra-high molecular weight polyethylene (UHMWPE) are placed in a gas impermeable pouch (such as polyethylene laminated aluminum foil), purged with a sensitizing gas and sealed with sensitizing gas substantially filling the package. The package is then heated to a temperature between room temperature and 90° C. The package is then irradiated at the heated temperature using e-beam or gamma irradiation.

Example 3

Warm Irradiation with Sensitizing Gas Below the Alpha Transition with Subsequent Annealing in Sensitizing Gas Test samples or a finished medical product of UHMWPE are place in a gas impermeable pouch (such as polyethylene laminated aluminum foil), purged with a sensitizing as and sealed with sensitizing gas substantially filling the package. The package is then heated to a temperature between room temperature and 90° C. The package is then irradiated at the heated temperature using e-beam or gamma irradiation. The package is then annealed at a temperature that is below the melting point of polyethylene.

Example 4

Warm Irradiation with Sensitizing Gas Above the Alpha Transition and Below the Melting Point Test samples of UHMWPE are placed in a gas impermeable pouch (such as polyethylene laminated aluminum foil), purged with a sensitizing gas and sealed with sensitizing gas substantially filling the package. The package is then heated to a temperature between 90° C. and melting temperature (about 145° C.). The package is then irradiated at the heated temperature using e-beam or gamma irradiation.

Example 5

Warm Irradiation with Sensitizing Gas Above the Alpha Transition and Below the Melting Point with Subsequent Annealing in Sensitizing Gas Test samples of UHMWPE are placed in a gas impermeable pouch (such as polyethylene laminated aluminum foil), purged with a sensitizing gas and sealed with sensitizing gas substantially filling the package. The package is then heated to a temperature between 90° C. and melting temperature (about 145° C.). The package is then irradiated at the heated temperature using e-beam or gamma irradiation. The package is then annealed at a temperature that is below the melting of point polyethylene.

Example 6

Post-irradiation Contacting with a 5%/95% Acetylene/Nitrogen Gas Blend at an Elevated Temperature to Reduce the Concentration of Residual Free Radicals GUR 1050 ram-extruded UHMWPE bar stock (3.5" diameter) was machined into 4 on which cylinders. The cylinders were irradiated using an Impela-10/50 AECL 10 MeV electron beam accelerator (E-Beam Services, Cranberry N.J.) to a dose level of 100 kGy in air. The irradiated cylinders were machine into 2 mm thick sections. Test samples were prepared using sections with dimensions of 3×3×2 mm. Test samples were placed in polyethylene laminated aluminum foil pouches (three test samples per pouch). Three of the pouches were purged with a 5% acetylene/95% nitrogen gas mixture (BOC Gas, Medford, Mass.) by pulling vacuum, then back-filling the pouch with the gas blend three times. The pouches were sealed and left in slightly positive pressure of the acetylene/nitrogen gas blend. A fourth pouch was purged using the same method with 100% nitrogen gas and sealed with a slightly positive pressure of nitrogen gas inside the package.

Two of the acetylene/nitrogen-filled pouches and the nitrogen-filled pouch were then placed in a convection oven at 100° C. for 24 hours. The other acetylene/nitrogen-filled pouch was kept at ambient temperature for 24 hours. The pouches were then opened, and the test samples were analyzed with electron spin resonance to determine the concentrate of residual free radicals in the specimens. A set of three additional test samples that were left in air at room temperature were also analyzed using electron spin resonance. Results are shown in Table 1.

The results show that the irradiated test samples left in the 5% acetylene/95% nitrogen gas blend at room temperature for 24 hours had substantial residual free radicals, as did the test samples stored in air at room temperature for 24 hours. The test samples left in the 100% nitrogen gas at 100° C. for 24 hours showed a slight decrease in residual free radical concentration. The test samples left in 5% acetylene/95% nitrogen gas blend at 100° C. for 24 hours had no substantially detectable residual free radical. Therefore, the addition of 5% acetylene into nitrogen is sufficient to reduce the concentration of the residual free radicals to undetectable levels following 100 kGy of electron beam irradiation.

Example 7

Irradiation of a Finished Polyethylene Medical Device in the Presence of a Sensitizing Gas at Room Temperature A medical device is prepared from conventional UHMWPE and packaged in a gas permeable material (such as Tyvek). It is then placed in gas impermeable packaging (such as foil laminated packaging). This package is then purged several times using a sensitizing atmosphere and was sealed in that atmosphere. The entire assembly is then irradiated using gamma irradiation or e-beam to a dose level of 1 to 1000 kGy. Following irradiation, the entire assembly is annealed. The annealing temperature is selected such that the packaging remains intact and that at least one level of hermetic seal between the outside and the component is not broken to maintain sterility of type medical device component. The component is then shipped for surgical use. If so desired, the remaining sensitizing gas is removed before shipping. The removal of the sensitizing gas is carried out by puncturing the package; or by removing the outer foil pouch and shipping the component in the gas permeable inner package.

Example 8

Reduction of Residual Free Radicals in a Finished Polyethylene Medical Device A medical device made out of polyethylene with residual free radicals is placed in a sensitizing atmosphere and annealed in the atmosphere that is below the melting point of the polyethylene in order to reduce the concentration of residual free radicals to at least substantially undetectable levels.

Example 9

Channel Die Deformation of Irradiated Polyethylene

Test samples of ultra-high molecular weight polyethylene are irradiated at room temperature using e-beam or gamma radiation. The samples are then placed in a channel die at 120° C., and are deformed in uniaxial compression defor-

TABLE 1

Concentration of residual free radicals measured in various specimens (n = 3 for all).

| Test sample | E-Beam Dose (kGy) | Post-Irradiation Environment | Post-Irradiation Temperature (° C.) | Annealing time (hrs) | Free radical concentration [$10^{15}$ spins/gram] |
|---|---|---|---|---|---|
| As-Is following irradiation | 100 | Air | 25 | Not applicable | 8.67 ± 2.1 |
| 100% Nitrogen environment. 100° C. for 24 hours | 100 | 100% nitrogen | 100 | 24 | 3.99 ± 1.1 |
| 5%/95% acetylene/nitrogen gas environment. room temperature | 100 | 5% acetylene | 25 | 24 | 9.70 ± 0.2 |
| 5%/95% acetylene/nitrogen gas environment, 100° C. for 24 hours FIRST RUN | 100 | 5% acetylene | 100 | 24 | Not detectable |
| 5%/95% acetylene/nitrogen gas environment, 100° C. for 24 hours REPEAT RUN | 100 | 5% acetylene | 100 | 24 | Not detectable |

Example 10

Channel Die Deformation of Irradiated Polyethylene contacted with a Sensitizing Environment Test samples of ultra-high molecular weight polyethylene are irradiated at room temperature using e-beam or gamma radiation. The samples are contacted with a sensitizing gas, such as acetylene until saturated. The samples are then placed in a channel die at 120° C., and are deformed in uniaxial compression deformation by a factor of 2. The residual free radical concentration, as measured with electron spin resonance, are compared with samples held at 120° C. for the same amount of time.

Example 11

Warm Irradiation with Mechanical Annealing

Test samples of ultra-high molecular weight polyethylene are irradiated at 120° C. adiabatically (that is, without significant heat loss to the environment) with electron beam radiation. The samples are then placed in a channel die at 120° C., and are deformed in uniaxial compression deformation by a factor of 2. The residual free radical concentration, as measured with electron spin resonance, is compared with samples held at 120° C. for the same amount of time.

Example 12

Post-Irradiation Annealing in the Presence of 5%/95% Acetylene/Nitrogen Gas Mixed at an Elevated Temperature to Reduce the Concentration of Residual Free Radicals in a Large Polyethylene Test Sample GUR 1050 ram-extruded UHMWPE bar stock (3.5"diameter) was machined into 4 cam thick cylinders. The cylinders were irradiated using an Impela-10/50 AECL 10 MeV electron beam accelerator (E-Beam Services, Cranberry, N.J.) to a dose level of 75 kGy in air. The irradiated cylinders were machined into test samples with dimensions of about 2×2×2 cm cubes. Two test samples were placed in two separate polyethylene laminated aluminum foil pouches. One pouch was purged with a 5% acetylene/95% nitrogen gas mixture (BOC Gas, Medford, Mass.) by pulling vacuum, then back-filling the pouch with the gas blend. The pouch was sealed and left in slightly positive pressure of the acetylene/nitrogen gas blend. The second pouch was purged using the same method with 100% nitrogen gas and sealed with a slightly positive pressure of nitrogen gas inside the package.

Both pouches were then placed in a convection oven at 133° C. for 24 hours. The pouches were then opened, and the test samples were further machined to prepare specimens for analysis with electron spin resonance. These specimens were prepared near the body center of the test samples.

The ESR analysis substantially no detectable free radicals in the specimen prepared from the irradiated polyethylene that was annealed while in contact with 5%/95% acetylene/nitrogen gas mixture. The specimen prepared from the test sample that was annealed in 100% nitrogen showed a free radical signal, which was quantified to represent $6 \times 10^{14}$ spins/gram.

This example shows that the presence of even low concentrations of a sensitizing gas such as 5% acetylene can reduce the concentration of residual free radicals in a large test sample with dimensions typical of a polyethylene orthopedic implant without heating the said test sample to above its melting point. This reduction in free radical concentration is more than what is obtained by subjecting the same irradiated polyethylene to an identical thermal history in the presence of 100% nitrogen.

Example 13

Post-Irradiation Mechanical Deformation at an Elevated Temperature to Reduce the Concentration of Residual Free Radicals GUR 1050 compression molded UHMWPE bar stock was machined into cubes of 4×4×4 cm dimensions. The cubes were irradiated using an gamma irradiation to a dose level of 75 kGy in nitrogen. The irradiated cubes were machine into test samples with dimensions of 2×2×1 cm. Two test samples were placed in an air convection oven and heated to 135° C. in air, overnight (about 10 hours or more). One of the test samples was then placed in aluminum channel die, which was heated to 135° C., and pressed to a compression ratio, $\lambda$, of about two. The pressure was then released and the sample was left to cool down to room temperature. The other test sample was simply removed from the convection oven and allowed to cool down to room temperature with no mechanical deformation.

Both of these test samples were further machined. The test sample that was subjected to heating only was cut to remove a 5 mm long sliver (about 2×2 mm cross-section) from the body center. The other sample that was subjected to heating and channel die compression was cut to remove a 5 mm long silver (about 2×2 mm cross-section) from the body center. The long-axis of the sliver was parallel to the channel die flow direction. Both of these slivers were then analyzed with electron spin resonance.

The ESR analysis showed a free radical signal (which was quantified to represent $2 \times 10^{15}$ spins/gram) in the sliver that was prepared from the test sample that was heated to 135° C. overnight. In contrast, the sliver prepared from the test sample that was heated to 135° C. and mechanically deformed in the channel die ($\lambda=2$) at that temperature showed no detectable residual free radicals. This example confirms that mechanical deformation at an elevated temperature reduces the concentration of residual free radicals.

Example 14

Determination of Crystallinity with Differential Scanning Calorimetry (DSC) Method Differential scanning calorimetry (DSC) technique was used to measure the crystallinity of the polyethylene test samples. The DSC specimens were prepared from the body center of the polyethylene test sample unless it is stated otherwise.

The DSC specimen was weighed with an AND GR202 balance to a resolution of 0.01 milligrams and placed in an aluminum sample pan. The pan was crimped with an aluminum cover and placed in the TA instruments Q-1000

Differential Scanning Calorimeter. The specimen was first cooled down to 0° C. and held at 0° C. for five minutes to reach thermal equilibrium. The specimen was then heated to 200° C. at a heating rate of 10° C./min.

The enthalpy of melting measured in terms of Joules/gram was then calculated by integrating the DSC trace from 20° C. to 160° C. The crystallinity was determined by normalizing the enthalpy of melting by the theoretical enthalpy of melting of 100% crystalline polyethylene (29Joules/gram). As apparent to the skilled person, other appropriate integration also can be employed in accordance with the teachings of the present invention.

The average crystallinity of three specimens obtained from near the body center of the polyethylene test sample is recorded with a standard deviation.

The Q1000 TA Instruments DSC is calibrated daily with indium standard for temperature and enthalpy measurements.

Example 15

Crystallinity Measurements of Polyethylene Following Irradiation and Channel Die Deformation at an Elevated Temperature GUR 1050 compression molded UHMWPE bar stock was machined into cubes of 4×4×4 cm dimensions. The cubes were irradiated using gamma irradiation to a dose level of 75 kGy in nitrogen. The irradiated cubes were machined into test samples with dimensions of 2×2×1 cm. One test sample (CIMA-12) was placed in an air convection oven and heated to 135° C. in air, overnight (10 hours). The test sample was then placed in an aluminum channel die, which was heated to 135° C., and pressed to a compression ratio, $\lambda$, of about two. The pressure was then released and the sample was left to cool down to room temperature.

The compressed test sample was further machined to prepare specimens from near the body center to be used to determine the crystallinity. Three such specimens obtained from near the body center were analyzed using a TA instruments Differential Scanning Calorimeter at a heating rate of 10° C./min and a temperature scan range of 0° C. to 200° C.

The enthalpy of melting (in terms of Joules/gram) was then calculated by integrating the DSC trace from 20° C. to 160° C. The crystallinity was determined by normalizing the enthalpy of melting by the theoretical enthalpy of melting of 100% crystalline polyethylene (291 Joules/gram).

The average crystallinity of the three specimens obtained from near the body center of the test sample was 58.9% with a standard deviation of 0.7.

Example 16

Free Radical Concentrations and Thermo-Oxidative Aging or Accelerated Aging Behavior of an Irradiated and Mechanically Deformed Polyethylene Sample GUR 1050 compression molded UHMWPE bar stock was machined into cubes of 4×4×4 cm dimensions. The cubes were irradiated using gamma irradiation to a dose level of 75 kGy in nitrogen. The irradiated cubes were machined into test samples with dimension of 2×2×1 cm. One test sample (CIMA-28) was placed in an air convection oven and heated to 135° C. in air for 4 hours. The test sample was then placed in an aluminum channel die, which was heated to 135° C., and pressed to a compression ratio, $\lambda$, of about two. The pressure was then released and the sample was put back into the air convection oven and heated for an additional 4 hours at 135° C. to recover most of the plastic deformation.

Figure 2:
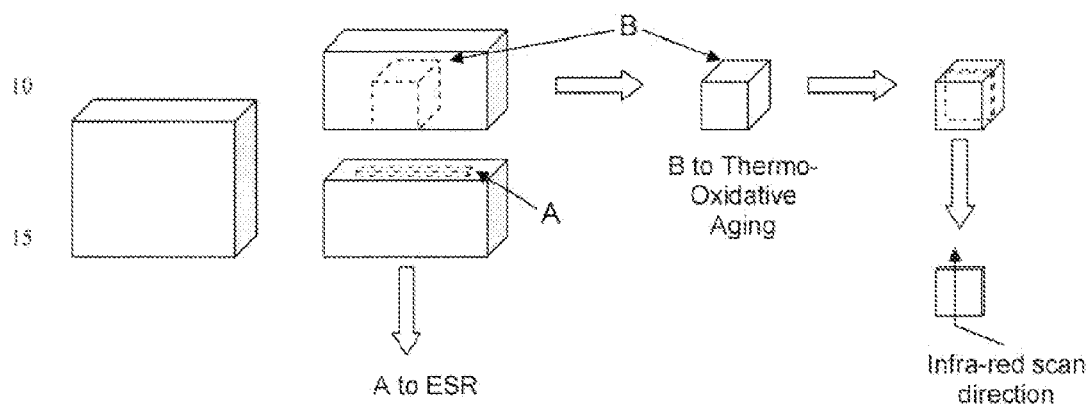
FIG. 2.

A specimen was prepared by cutting a 3×3×10 mm piece near the body center with long axis of the specimen in the flow direction of the channel die (see A in FIG. 2). The specimen was analyzed with electron spin resonance and no free radicals were detected. The remaining half of the test sample was further machined to obtain a cube with dimensions of 1×1×1 cm. This cubic specimen (see B in FIG. 2) was then subjected to thermo-oxidative aging or accelerated aging in air convection oven at 80° C. for three weeks. This method of aging will induce oxidation in the polyethylene if there are residual free radicals. At the completion of the aging, the cubic specimen was cut in half and microtomed to remove a 200 micrometer thin section. The section was then analyzed using a BioRad UMA500 infra-red microscope as a function of depth away from the edge of the microtomed section as shown in FIG. 2. The infra-red spectra collected with this method showed no detectable carbonyl vibration throughout the microtomed section, indicating no detachable oxidation. The crystallinity of the aged test sample was also determined using three specimens cut form the said aged test sample using the DSC method described above in Example 14. The crystallinity of the three specimens averaged 59.2% with a standard deviation of 0.9 when the melting enthalpy was calculated by integrating the DSC trace from 20° C. to 160° C.

The aging method provided additional support for the electron spin resonance in showing that irradiation followed by mechanical deformation at an elevated temperature results in a marked reduction in the concentration of residual free radicals and an increase in thermo-oxidative stability of irradiated polyethylene.

Example 17

Annealing Following Free Radical Reduction Using Channel Die Compression at an Elevated Temperature GUR 1050 UHMWPE bar stock was irradiated with gamma rays to 75 kGy in nitrogen. The irradiated block was then machined to blocks with dimensions of 2×2×1 cm. Two of these blocks were placed in an air convection oven at 133° C. for 4 hours. Both of these heated blocks were then compressed in a channel die that was heated to 133° C. The compression ratio, $\lambda$=initial height/final height, was about two. The dimensions of these blocks were measured and recorded after they were cooled down to room temperature (see Table 2).

One of the blocks (Block I in Table 2) was then annealed under no load at 135° C. for 16 hours and cooled down to room temperature. Following this annealing cycle the dimensions of the block were measured again as shown in the Table 2. This observation shows that the plastic deformation was markedly recovered by annealing below the melting point.

The other block (Block II in Table 2) was annealed under no load at 150° C. for 6 hours and cooled down to room temperature. Following this annealing cycle the dimensions of the block were measured again as shown in Table 2. This observation shows that plastic deformation is almost fully recovered by annealing above the melting point.

TABLE 2

Annealing below and above melt using channel die compression at an elevated temperature.

*Dimensions CD/FD/WD (mm)

| Sample | Initial (mm) | Following channel die compression | Following Annealing |
|---|---|---|---|
| Block I (Annealed below the melt) | 20 × 20 × 9.5 | 12 × 35 × 10 | 16.5 × 23.5 × 9.5 |
| Block II (Annealed above the melt) | 20 × 20 × 9.5 | 10 × 40 × 10 | 20 × 20 × 9 × 5 |

*CD—Compression Direction; FD—Flow Direction; WD—Wall Direction

Example 18

Thermal Oxidative or Accelerated Aging Behavior of Irradiated Cross-Linked Polyethylenes That Are Heated and Mechanically Deformed Versus an Irradiated Cross-Linked Heated Polyethylene GUR 1050 UHMWPE bar stock was machined into blocks that were 9×9×4 cm. The blocks were gamma irradiated in a vacuum package to 100 kGy. Blocks were subsequently machined into the 19 mm cubes.

Four groups of cubes (n=2 for each temperature) were heated for one hour at 125° C., 128° C., 132° C., or 135° C., respectively. Subsequently, each heated cube was mechanically deformed between two flat aluminum plates held at room temperature to a compression ratio, λ, of 4.5. The compression displacement was held at this point for 5 minutes to allow for stress relaxation to occur. The load required to hold the displacement constant at this point was monitored. By the end of the five minutes the load had decreased and reached steady state, at which point the sample was removed from the press. All deformed cubes were then annealed at 135° C. for 1 hour to partially recover deformation. Samples were then machined in half in the direction of compression to expose an internal surface for accelerated aging.

Another four groups of cubes (n=2 for each group) were prepared to serve as thermal controls with no deformation history. These cubes were subjected to the same thermal histories as those of the four groups described above. That is, the four groups were heated for one hour at 125° C., 128° C., 132° C., or 135° C., respectively. The cubes were then allowed to cool down to room temperature and annealed at 135° C. for 1 hour. The thermal control samples were then machined in half in the direction of compression to expose an internal surface for accelerated aging.

The accelerated aging test specimens were placed in an air convection oven at 80° C. and aged for 6 weeks. At the completion of aging, the samples were cut in half and a 200 μm thin section was removed. The thin section was scanned using a BioRad UMA 500 infrared microscope at 100 micrometer intervals as a function of distance away from the exposed internal free surface that was in contact with air during aging. The scans were used to find the location of the maximum carbonyl vibration. The infrared spectrum collected at this maximum location was used to assign an oxidation index to that aged cube. The oxidation in index was calculated by normalizing the area under the carbonyl vibration to that under the 1370 $cm^{-1}$ vibration. The higher the oxidation in the sample, the stronger is the carbonyl vibration and as a result higher is the oxidation index.

The oxidation indexes of the four groups of deformed samples were less than 0.03. In contrast, the thermal control groups showed oxidation indexes of 1.3, 1.2, 1.2, and 1.3 for the pre-heat temperatures of 125° C., 128° C., 132° C., or 135° C., respectively.

Based on above results, it is concluded that heating along (below the melting point) does not improve the oxidation resistance of irradiated and cross-linked polyethylene to the same extent as heating and subsequent deformation do.

It is to be understood that the description, specific examples and data, while indicating exemplary aspects, are given by way of illustration and are not intended to limit the present invention. Various changes and modifications within the present invention will become apparent to the skilled artisan from the discussion, disclosure and data contained herein, and thus are considered part of the invention.

The invention claimed is:

1. An irradiated crosslinked polyethylene composition made by a process comprising steps of:
    a) irradiating polyethylene at a temperature that is below the melting point of the polyethylene;
    b) mechanically deforming the polyethylene from step a) at a temperature that is above room temperature and below the melting point of the irradiated polyethylene in order to reduce the concentration of residual free radicals; and
    (c) allowing the polyethylene from step b) to cool following the deformation.

2. The irradiated crosslinked polyethylene composition of claim 1, wherein the mechanical deforming is by pressure.

3. The irradiated crosslinked polyethylene composition of claim 2, wherein the polyethylene from step a) is pressed to a compression ratio of 2.

4. The irradiated crosslinked polyethylene of claim 2, wherein following the release of the pressure, the polyethylene is allowed to cool to room temperature.

5. The irradiated crosslinked polyethylene of claim 1, wherein the mechanical deformation is conducted at a temperature between 100° C. to 137° C.

6. The irradiated crosslinked polyethylene of claim 1, wherein the mechanical deformation is conducted at a temperature between 120° C. to 137° C.

7. The irradiated crosslinked polyethylene of claim 1, wherein the mechanical deformation is conducted at a temperature between 130° C. to 137° C.

8. The irradiated crosslinked polyethylene of claim 1, wherein the mechanical deformation is conducted at a temperature of about 135° C.

9. A medical device comprising a polyethylene component made by a process comprising steps of:
    a) irradiating polyethylene at a temperature that is below the melting point of the polyethylene, thereby forming a crosslinked polyethylene;
    b) mechanically deforming the crosslinked polyethylene at a temperature that is above room temperature and below the melting point of the crosslinked polyethylene, in order to reduce the concentration of residual free radicals and then allowing the polyethylene to cool;
    c) annealing the mechanically deformed crosslinked polyethylene by heating to a temperature below the melting point of the crosslinked polyethylene in order to permit shape recovery;
    d) machining the annealed mechanically deformed crosslinked polyethylene, thereby forming a component;

e) assembling the medical device comprising the component;

f) packaging the medical device; and g) sterilizing the packaged device.

10. The medical device of claim 9, wherein radiation dose level is between about 1 and about 1,000 kGy.

11. The medical device of claim 9, wherein radiation dose level is between about 25 and about 125 kGy.

12. The medical device of claim 9, wherein the deformed polyethylene is crystallized at the deformed state.

13. The medical device of claim 9, wherein the crosslinked polyethylene has substantially no trapped residual free radical detectable by electron spin resonance.

14. The medical device of claim 9, wherein crystallinity of the crosslinked polyethylene is at least about 51%.

15. The medical device of claim 9, wherein the mechanical deformation mode is selected from the group consisting of channel flow, uniaxial compression, biaxial compression, oscillatory compression, uniaxial tension, biaxial tension, ultra-sonic oscillation, bending, plane stress compression (channel die), and combinations thereof.

16. The medical device of claim 9, wherein the polyethylene is ultra-high molecular weight polyethylene (UHMWPE).

17. The medical device of claim 9, wherein the deforming temperature and the annealing temperature are less than about 140° C.

18. The medical device of claim 9 is a medical prosthesis.

19. The medical device of claim 9 is an acetabular liner or a knee insert.

20. The medical device of claim 9 is a finished medical device.

21. The medical device of claim 9, wherein the annealing is carried out for at least about a week.

22. The medical device of claim 9, wherein the annealing is carried out for at least about a 2 days.

23. A medical device comprising a polyethylene component made by a process comprising steps of:

a) irradiating polyethylene at a temperature that is below the melting point of the polyethylene, thereby forming a crosslinked polyethylene;

b) mechanically deforming the crosslinked polyethylene at a temperature that is above room temperature and below the melting point of the crosslinked polyethylene, in order to reduce the concentration of residual free radicals;

c) annealing the mechanically deformed crosslinked polyethylene in a sensitizing environment at a temperature below the melting point of the crosslinked polyethylene in order to permit shape recovery;

d) machining the annealed mechanically deformed crosslinked polyethylene, thereby forming a component;

e) assembling the medical device comprising the component;

f) packaging the medical device; and g) sterilizing the packaged device.

24. The medical device of claim 23, wherein the polyethylene is ultra-high molecular weight polyethylene (UHMWPE).

25. The medical device of claim 23, wherein radiation dose level is between about 1 and about 1,000 kGy.

26. The medical device of claim 23, wherein radiation dose level is between about 25 and about 125 kGy.

27. The medical device of claim 23, wherein the deforming or the annealing temperature is less than about 140° C.

28. The medical device of claim 23, wherein the sensitizing environment comprises acetylene.

29. The medical device of claim 23, wherein the sensitizing environment comprises about 5% by volume acetylene and about 95% by volume nitrogen.

30. The medical device of claim 23 is a medical prosthesis.

31. The medical device of claim 23 is an acetabular liner or a knee insert.

32. The medical device of claim 23 is a finished medical device.

33. A medical device comprising a polyethylene component, wherein the polyethylene component is made by the process comprising steps of:

a) irradiating the polyethylene in an inert environment at a temperature that is above room temperature and below the melting point of the polyethylene; and b) contacting the polyethylene with a sensitizing environment in order to reduce the content of free radicals.

34. The medical device of claim 33, wherein the polyethylene is ultra-high molecular weight polyethylene (UHMWPE).

35. The medical device of claim 33, wherein the radiation dose level is between about 1 and about 1,000 kGy.

36. The medical device of claim 33, wherein the radiation dose level is between about 25 and about 125 kGy.

37. The medical device of claim 33, wherein the polyethylene is irradiated to 75 kGy.

38. The medical device of claim 33, wherein irradiation is carried out in air or an inert environment.

39. The medical device of claim 33, wherein the medical device is a medical prosthesis.

40. The medical device of claim 33, wherein the medical device is an acetabular liner or a knee insert.

41. The medical device of claim 33, wherein the medical device is a finished medical device.

42. The medical device of claim 33, wherein the sensitizing environment comprises about 5% by volume acetylene and about 95% by volume nitrogen.

43. The medical device of claim 33, wherein the sensitizing environment comprises acetylene.

44. The medical device of claim 9, wherein the mechanical deformation mode is selected from the group consisting of uniaxial, tension, and combinations thereof.

* * * * *